United States Patent [19]

McKean et al.

[11] Patent Number: 4,960,999
[45] Date of Patent: Oct. 2, 1990

[54] SCANNING AND STORAGE OF ELECTROPHORETIC RECORDS

[75] Inventors: Ronald A. McKean, Royal Oak; Jeff Stiegman, Ann Arbor, both of Mich.

[73] Assignee: KMS Fusion, Inc., Ann Arbor, Mich.

[21] Appl. No.: 309,104

[22] Filed: Feb. 13, 1989

[51] Int. Cl.$^5$ ................. G01N 21/64; G01N 27/26
[52] U.S. Cl. ................. 250/461.1; 250/458.1; 204/299 R
[58] Field of Search ............ 250/461.1, 458.1; 204/299 R, 182.8, 180.1

[56] References Cited

U.S. PATENT DOCUMENTS 4,726,904  2/1988  Ayers ........................ 204/182.7
4,874,492 10/1989  Mackay ...................... 204/299 R

FOREIGN PATENT DOCUMENTS 0294524 12/1988 European Pat. Off. ........ 204/299 R

Primary Examiner—Janice A. Howell
Assistant Examiner—Richard Hanig
Attorney, Agent, or Firm—Barnes, Kisselle, Raisch, Choate, Whittemore & Hulbert

[57] ABSTRACT

An electrophoretic record that includes at least one gel separation is mounted for motion laterally of the separation record. A light source is positioned to illuminate at least a portion of the record, and a linear array camera is positioned to have a field of view of the illuminated portion of the record and orthogonal to the direction of record motion. The elements of the linear array are scanned at increments of motion of the record across the field of view to develop a series of signals corresponding to intensity of light at each element at each scan increment.

31 Claims, 3 Drawing Sheets

SCANNING AND STORAGE OF ELECTROPHORETIC RECORDS

The present invention is directed to analysis of electrophoretic records, and more specifically to a method and apparatus for scanning and digital storage of electrophoretic DNA separations.

BACKGROUND AND OBJECTS OF THE INVENTION

In electrophoretic processes for separation of DNA components, DNA samples are placed in one or more wells located along one side edge of a thin rectangular gel plate. A voltage is applied to the gel, causing the DNA molecules to migrate out of the wells and travel laterally of the plate in the direction of applied voltage. Relative migration rates are determined largely by DNA component molecular weights, with molecules of lesser weight migrating more rapidly than molecules of greater weight. When completed after a predetermined time duration, the DNA samples are separated in a ladder series of bands extending laterally from the plate edge along which the sample wells are located. Each band contains DNA components of a specific molecular weight. Analysis therefore requires precise measurement of migration distant of, and molecular concentration within, the various bands.

Conventional techniques for analysis of electrophoretic records of the type described above typically contemplate use of dyes to facilitate optical analysis. For example, ethidium bromide is a fluorescent dye that is conventionally employed to facilitate analysis of DNA component concentration as a function of fluorescence of the individual bands under ultraviolet light. However, conventional analysis techniques, typically involving photographic recording of the fluorescing gel record, require extended exposure of the gel record, resulting in a record degradation. Specifically, conventional photographic procedures involve placement of the gel record on a transilluminating ultraviolet light table. Fluorescence is photographed using a suspended filter-equipped camera. While on the transilluminator, the gel is completely irradiated with ultraviolet light. Heat generated by the light causes the DNA to spread within the gel, resulting in loss of definition. Furthermore, the ultraviolet light itself causes damage to the DNA within the gel. This is a particularly serious problem when the DNA is to be recovered for other uses.

The photographic record is a second-generation record, which adds a source of error, not to mention time and expense, to the analysis process. Photographic measurements produce non-linear photometric results. This makes measuring DNA concentration very difficult. Furthermore, photographic film records require manual analysis, a process that is necessarily highly dependent upon training and skill of the technician. Thus, prior art techniques are at best amenable to qualitative analysis of electrophoretic DNA separation records, but are not readily amenable to precise quantitative analysis.

Another problem that inheres in prior art electrophoretic record analysis techniques lies in calibration of individual records and comparative analysis among a plurality of records. Because the analysis techniques are highly dependent upon skills of individual technicians, such records do not readily lend themselves to direct qualitative or quantitative comparison. Furthermore, the prior art has yet to propose an economical and reliable technique for quantitatively digitizing electrophoretic records for manipulation, analysis, and long term storage and retrieval in a digital computer.

It is therefore a general object of the present invention to provide a method and apparatus for analyzing electrophoretic DNA separations of the subject character that are economical to implement, that may be readily employed in both clinical and research applications by relatively unskilled personnel, and that facilitate quantitative analysis of DNA separations directly from the stained DNA in the gel separations themselves without intermediate photographic recording steps and the like.

Another and more specific object of the present invention is to provide a method and apparatus of the described character for scanning and converting electrophoretic records into digital format in which the records may be readily electronically manipulated and analyzed. Yet another object of the invention is to provide a method and apparatus of the described character that include facility for compensating the digital record against effects of background radiation and variations in scanning illumination intensity, such that normalized records may be employed directly for purposes of comparative analysis.

A further object of the invention is to provide apparatus for scanning and recording electrophoretic gel separation records of the subject type that includes facility for controlling scanning resolution, is readily adaptable for use in conjunction with electrophoretic gel separations of a variety of types, and that features a compact and modular design.

SUMMARY OF THE INVENTION

An electrophoretic record that includes at least one gel separation is mounted for motion in a predetermined direction with respect to the separation record, preferably laterally of the direction of gel separation. A light source is positioned to illuminate at least a portion of the record, and a linear array camera is positioned to have a field of view of the illuminated portion of the record and orthogonal to the direction of record motion. The elements of the linear array are scanned at increments of motion of the record across the field of view to develop a series of signals corresponding to intensity of light at each element at each scan increment, and the element intensity signals are electronically stored for later retrieval and analysis. In the preferred embodiment of the invention, such electronic storage includes conversion of the array intensity signals from analog to digital format, and storage of the digitized signals in digital memory as a function of increments of record motion.

The light source in the preferred embodiment of the invention includes an enclosure having an elongated window and a light emitter, such as a tubular ultraviolet lamp, positioned to direct light through the window. Most preferably, the camera field of view is projected onto the record through the illumination window, with the lamp being positioned off-axis with respect to the camera field of view so that the scanned image excludes the bulb. A shield is spaced from the window at a position to permit translation of a record between the window and shield, and to reflect any ultraviolet light that passes through the record back into the record for enhanced excitation of fluorescence. Blocking filters prevent transmission of ultraviolet light and other non-UV noise components, passing only image components within a selected spectral envelope to the camera linear array. The shield may include a window for transmission of visible light to permit observation of record fluorescence.

In accordance with one aspect of a presently preferred embodiment of the invention herein disclosed, a calibration filter of generally uniform optical characteristics is selectively illuminated by the light source at a position within the camera field of view. Fluorescence from the calibration filter is imaged through the scan window onto the entire linear array device. Ideally, each element of the array would indicate the same intensity. However, due to optical non-uniformity and detector sensitivity variances, such may not be the case. Signals from each camera array element are employed to determine a gain factor for each element as a function of differences among the element intensity signals to normalize the response when the calibration filter is scanned by the camera. Thereafter, during scanning of electrophoretic records, signals from each element are multiplied by the associated gain factor prior to digital storage. Furthermore, background illumination noise is identified during the calibration operation, and signals from the array elements are correspondingly offset during the record scanning operation.

BRIEF DESCRIPTION OF THE DRAWINGS

The invention, together with additional objects, features and advantages thereof, will be best understood from the following description, the appended claims and the accompanying drawings in which:

DETAILED DESCRIPTION OF PREFERRED EMBODIMENT

Figure 1:
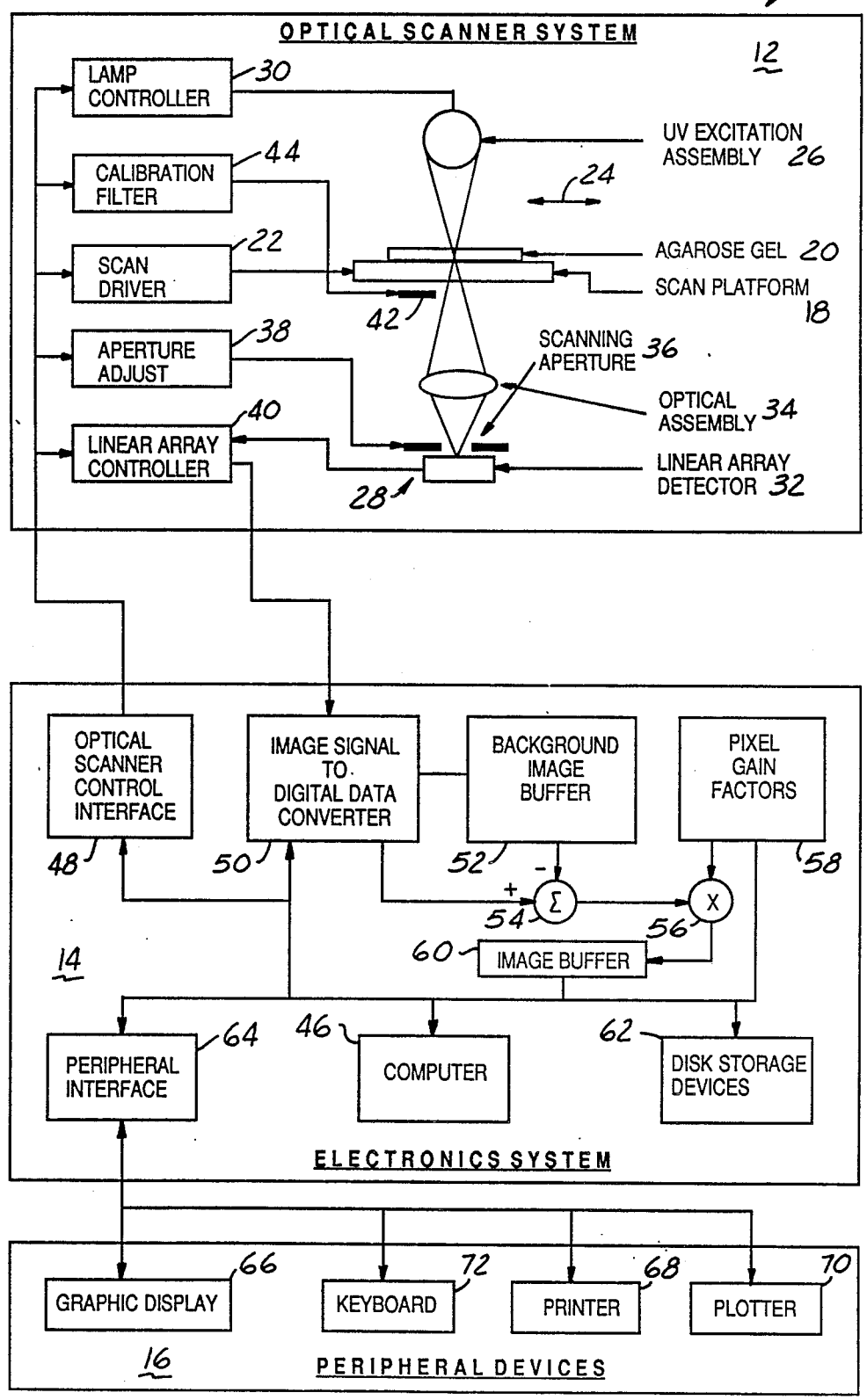
FIG. 1 is a functional block diagram of apparatus for scanning and digitally storing electrophoretic gel separation records in accordance with a presently preferred embodiment of the invention.
Figure 3:
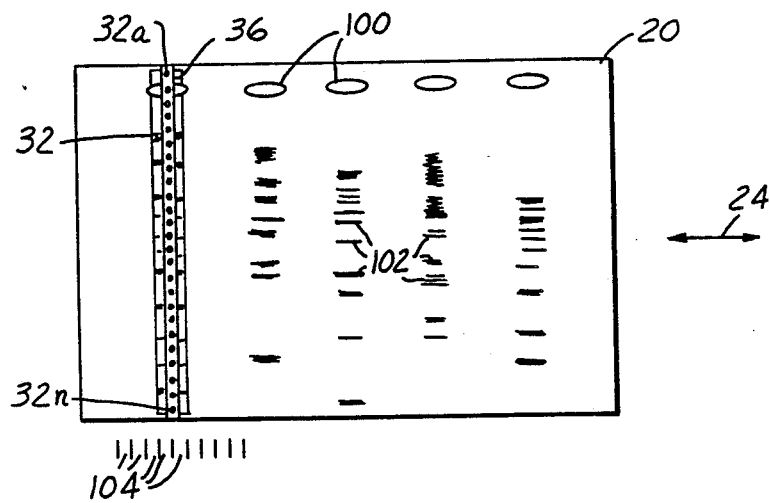
FIG. 3 is a schematic diagram of an electrophoretic record, with linear array camera field of view superimposed thereon, in accordance with a presently preferred implementation of the invention.

FIG. 1 illustrates an apparatus 10 in accordance with a presently preferred embodiment of the invention as comprising an optical scanner module 12 coupled to an electronics module 14. Module 14 includes facility for controlling scanner module 12 as well as storage of data obtained therefrom, and is coupled to one or more peripheral devices 16 for display of electrophoretic record data and implementation of operator control. Optical scanner module 12 includes a scan platform 18 contoured to receive and hold a gel separation record 20. Platform 18 is coupled to a scan driver 22 for translating record 20 in the direction 24 between a light source 26 and a camera 28. Camera 28 includes a linear array detector 32 onto which the image of the illuminated portion of record 20 is projected by a lens assembly 34 through a scanning aperture 36 (FIGS. 1 and 3), such that the field of view of detector 32, illustrated in FIG. 3, is orthogonal to direction 24 of translation of record 20. Scanning aperture 36 is adjustably controlled by appropriate mechanical means and/or electronics 38. Linear array detector 32 includes plurality of light-responsive elements ($32a$–$32n$ in FIG. 3) that receive image information simultaneously through the scanning aperture and provide associated electronic signals to a linear array scan controller 40 as an integrated function of intensity of light received between scans at the individual detector elements. A calibration filter 42 is selectively positionable by associated control mechanical means and/or electronics 44 between lamp 26 and detector 32 for calibrating the detector and electronics module, as will be described.

Electronics module 14 includes a computer 46 that controls operation of optical scanner module 12 through a scanner control interface 48. The individual image or pixel signals at detector 32 are fed by linear array controller 40 to an input electronics package 50. Input package 50 includes facility for analog-to-digital conversion of input signals under control of computer 46. Outputs from electronics package 50 are fed to a background image buffer 52, and to a summer 54 that receives an offset input from buffer 52. The output of summer 54 is fed to a multiplier 56 controlled by the pixel gain storage electronics 58. The output of multiplier 56 is fed to an image buffer 60, and thence under control of computer 46 to digital storage 62, such as a suitable disk storage devices. Scanned and/or stored record data may also be fed through a peripheral interface 64 to one or more peripheral devices 16, which may include a graphic display 66, a printer 68 and a plotter 70. Devices 16 also include a keyboard 72 for operator control of electronics module 14 and optical scanner module 12.

Figure 2:
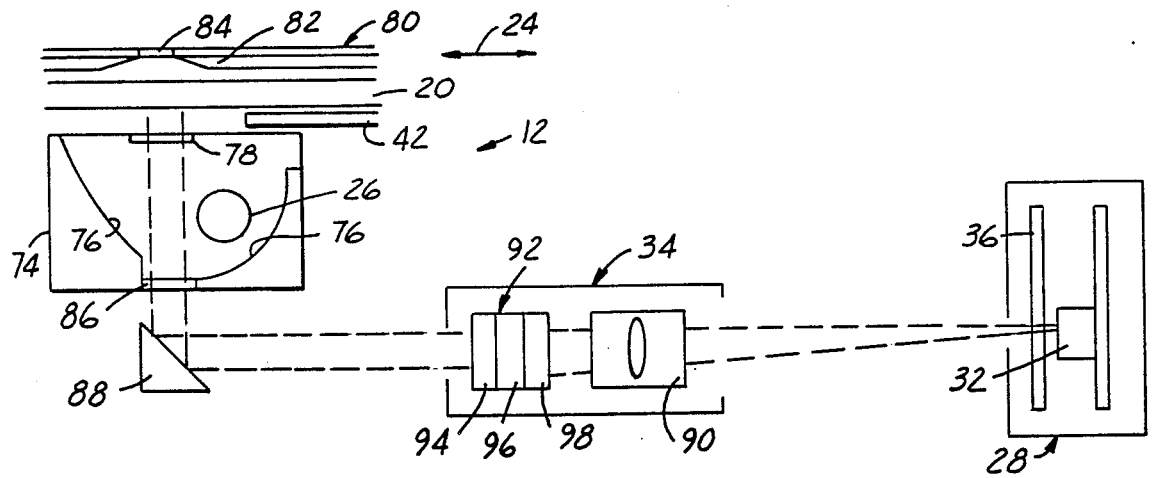
FIG. 2 is a schematic diagram of the optical scanner in the system of FIG. 1.

FIG. 2 illustrates the optical components of scanner module 12 in accordance with a presently preferred embodiment of the invention. Lamp 26 is positioned within an enclosure 74 that includes the elliptical reflecting surfaces 76 for directing light energy from lamp 26 through an elongated (into the page of FIG. 2) generally rectangular scan window 78. In an exemplary but presently preferred implementation of the invention for scanning flourescently-labeled electrophoretic DNA separations in agarose gels, lamp 26 comprises a low pressure tubular mercury gas bulb energized by a controller 30 to emit ultraviolet energy centered about a peak wavelength of 302 nm. The tubular light source is placed at one focus of elliptical reflector 76, and the illuminated gel strip is located at the other reflector focus. A scan shield 80 is spaced from scan window 78, a gap being provided between enclosure 74 and shield 84 for translation of a gel record 20 therebetween. Shield 80 includes an ultraviolet reflector 82 opposed to enclosure 74, and an elongated viewing window 84 opposed to window 78 for observation of fluorescence in the visible light region. A second window 86 is carried by enclosure 74 in opposed alignment with window 78, and is comprised of material that blocks transmission of ultraviolet radiation but permits transmission of radiation in the visible region of the spectrum. Thus, ultraviolet radiation is contained within enclosure 74, and in the region between enclosure 74 and shield 80.

Visible light transmitted through window 86, caused by ultraviolet-excited fluorescence of record 20, is reflected by a mirror 88 through lens assembly 34 and through scanning aperture 36 onto array detector 32. Lens assembly 34 includes a wide angle lens 90 and a series of spectral selectivity filters 92. Filters 92 block not only ultraviolet radiation at the wavelength of lamp 26, but also other non-UV noise components outside of the selected spectral envelope of interest. This envelope can vary depending upon instrument application. In a presently preferred embodiment of the invention for use with ethidium bromide dye, filters 92 include a heat-absorbing filter 94, a colored glass cutoff filter 96 and a broadband cutoff filter 98 that cooperate to transmit light onto array detector 32 only in a relatively narrow band between 590 nm and 620 nm. It will be noted in FIG. 2 that lamp 26 is positioned off-axis with respect to the path of transmission of visible light energy onto detector 32, so that the image projected onto detector 32 does not include light source lamp 26.

In operation, calibration filter 42 is first positioned so as to be illuminated by lamp 26. Filter 42 possesses substantially uniform optical characteristics and, in a preferred implementation of the invention, fluoresces orange when exposed to ultraviolet radiation. The elements of array 32 are scanned, and the outputs thereof are compared to each other at computer 46 to develop a gain factor or constant for each element pixel signal so as to normalize the output signals to some predetermined level. These gain factors are then stored in circuit 58 (FIG. 1). Likewise, data associated with background light and other noise factors is stored in buffer 52 to offset image data during a scan operation.

Following the calibration procedure, a flourescently labeled electrophoretic gel separation record 20 is positioned on scan platform 18. As illustrated in FIG. 3, record 20 preferably comprises a number of DNA wells 100 from which DNA molecules have migrated under electrophoretic voltage to form a plurality of bands 102 orthogonal to direction 24 of record translation, and thus parallel to the field of view of detector array 32. Lamp 26 is then energized and record 20 is translated in direction 24. Detector 32 is scanned at increments 104 of translation in direction 24, and pixel signals from each element in detector array 32 are digitized and stored, first in image buffer 60 and then in computer 46 and/or disk storage device 62 (FIG. 1). Motion in direction 24 may be either continuous with a suitable device for sensing increments 104 (FIG. 3) of motion, or step wise in uniform increments 104.

Thus, there is stored in memory digital information indicative of light intensity at each array pixel 32a-32n (FIG. 3) at each scan increment 104. Since each such intensity reading is a direct function of fluorescence at a point on the record illuminated by bulb 26 and viewed by the associated array element, which in turn is a direct function of DNA molecular concentration at such point, the scanned and stored electronic record provides a direct quantitative measure of DNA concentration and separation in the electrophoretic record. Moreover, normalization and offset of the pixel signals, as a result of the calibration operation previously discussed, facilitates direct comparison between and among electrophoretic records, even when prepared by different technicians under differing conditions. Control of scan aperture permits selective control of image resolution at the array. Use of a 2048 element linear array detector 32 in a preferred embodiment of the invention may yield a pixel width of 0.012 mm and a resolution of 0.1 mm in the direction of electrophoretic migration.

Figure 4:
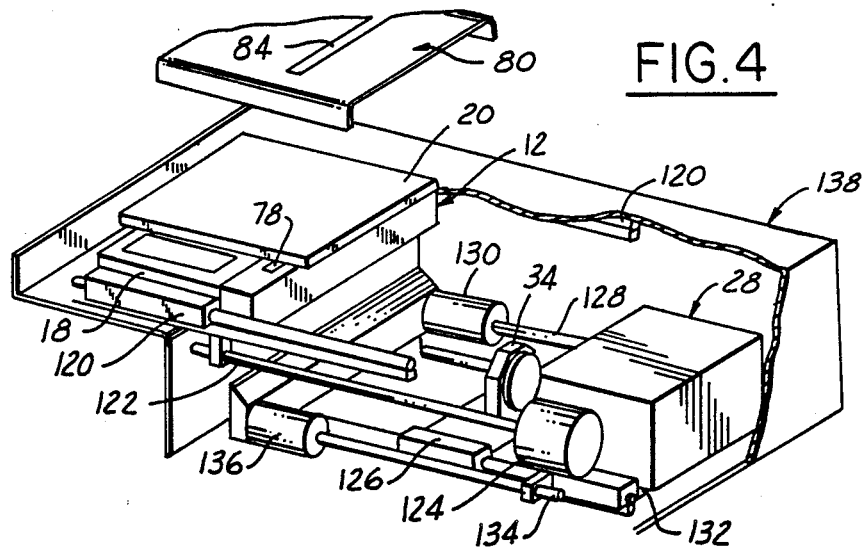
FIG. 4 is a fragmentary partially exploded perspective view of a scanner in accordance with a presently preferred embodiment of the invention.

FIG. 4 illustrates one embodiment of the scanner shown functionally in FIG. 1 and schematically FIGS. 2-3. Scan platform 18 is mounted on a low-friction slide 120 that is coupled by a lead screw 122 to a gel scan stepper motor 124. Lens and filter assembly 34 is likewise mounted on a platform 126 that is coupled through a lead screw 128 to an optics positioning stepper motor 130. Camera 28 is carried on a slide platform 132 that is coupled by a lead screw 134 to a camera positioning stepper motor 136. The optics and motors are positioned within an enclosure 138 from which platform 18 extends to receive a gel record 20. Shield 80 is removably positionable over platform 18.

Figure 5:
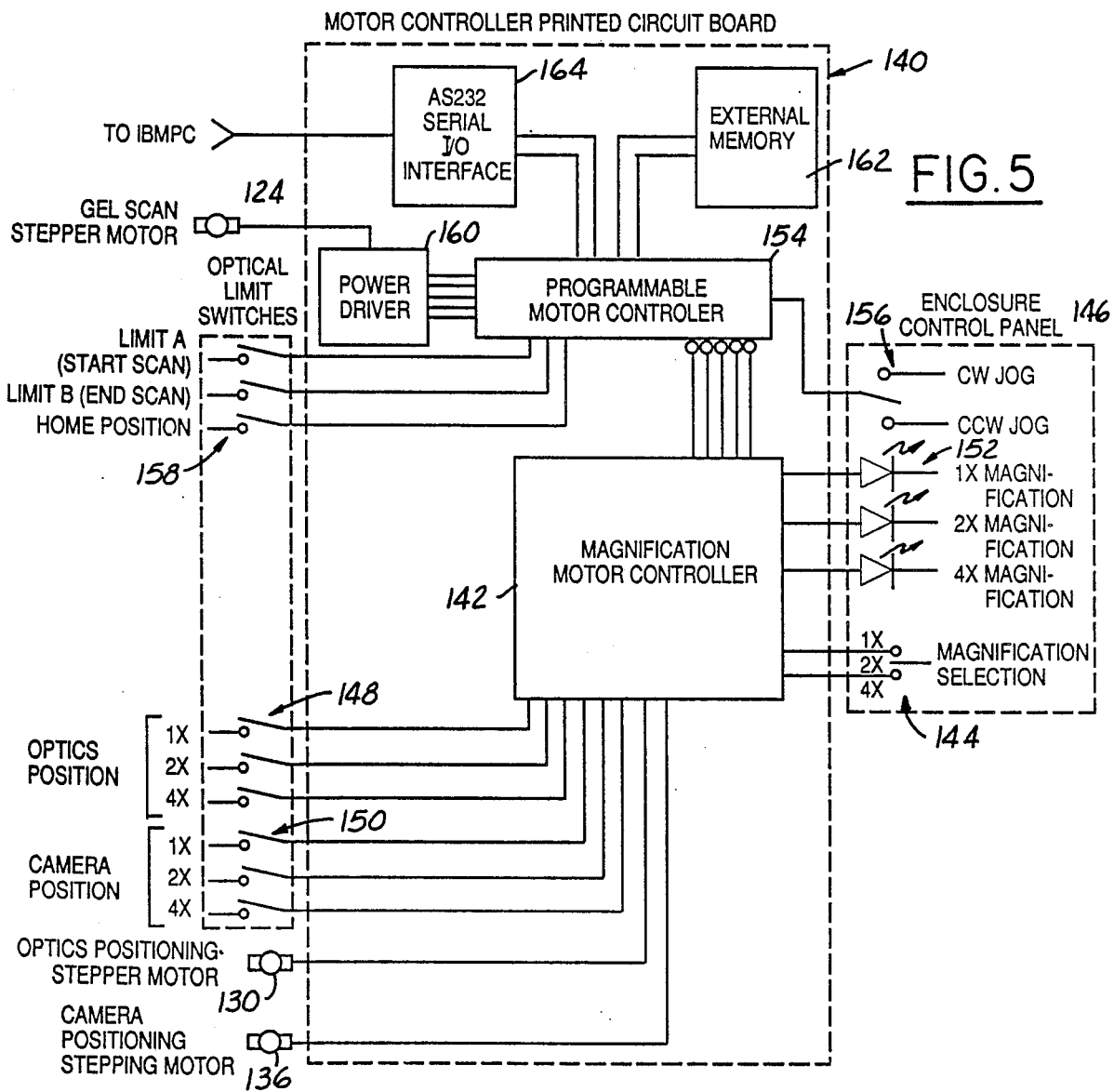
FIG. 5 is a functional block diagram of the scanner motor control electronics in the embodiment of FIG. 4.

FIG. 5 illustrates the motor control electronics 140 in the embodiment of FIG. 4 as comprising a magnification controller 142 that receives an input from a three-position magnification selection switch 144 mounted on an operator panel 146 on enclosure 138 (FIG. 4). Controller 142 drives optics positioning stepper motor 130 (FIGS. 4 and 5) and camera positioning stepper motor 136 to drive the lens assembly 34 and camera 28 to respective positions corresponding to operator-selected magnification. A series of limit switches 148 are positioned within enclosure 138 (FIG. 4) and responsive to position of optics slide 126 for indicating positioning to the optics slide at the predetermined magnification positions. Likewise, a series of limit switches 150 are positioned within the instrument cabinet and responsive to position of camera slide 132 at the preset camera magnification positions. Limit switches 148, 150 are connected to magnification motor controller 142. Controller 142 also drives LEDs 152 on panel 146 to indicate placement of the optics and camera at the positions for desired magnification selected by the operator through switch 144.

A programmable motor controller 154 receives an input from a three-positioned switch 156 on panel 146 for selectively jogging scan platform 18. Controller 154 also receives inputs from a series of limit switches 158 that are positioned within enclosure 138 and responsive to scan platform 18 for indicating respective limit positions, and also a predetermined "home" position from which a scanning operation commences. Controller 154 also receives inputs from magnification motor controller 142, and drives gel scan stepper motor 124 through a power driver 160. Controller 154 is also connected to an on-board memory 162, and to a serial I/O interface 164 for communication with an external computer or the like.

The modular optical scanner illustrated in FIGS. 1, 2 and 4 embodies a number of advantages over prior art devices. In addition to the many structural and functional advantages already mentioned, it will by noted that the excitation source does not hinder observation of the gel during scanning Indeed, although shield 80 protects operators from potentially harmful ultraviolet emissions, fluorescence in the visible region may be viewed directly through window 84. The gel record may be easily accessed regardless of its scan position. Scan window 78 may be easily accessed for periodic cleaning. Ultraviolet light passaging through the gel record is reflected by shield reflector 82 back into the gel for enhanced absorption and fluorescence efficiency. Shield 80 also helps block background light from being imaged onto camera detector 32, and thus helps reduce background noise while increasing sensitivity. The gel is irradiated by a narrow linear light source, thus resulting in reduced heat degradation as compared with prior art devices. Furthermore, there is minimal radiation-induced damage to the gel record. Modular construction of the subject scanner facilitates modification for specific applications. For example, the light source and filters may be readily replaced for use in conjunction with other types of dyed gel records. The light source may be placed above the gel, allowing overhead excitation.

The invention claimed is:

1. Apparatus for analyzing an electrophoretic record that includes at least one gel separation, said apparatus comprising:
   means for mounting the record and moving the record in a predetermined direction with respect to the separation on the record,
   a light source positioned with respect to said record-mounting means to illuminate at least a portion of the record,
   a camera comprising a plurality of light-responsive elements disposed in a linear array positioned with respect to said mounting means such that said camera has a linear field of view of a portion of the record on said mounting means illuminated by said light source and orthogonal to said predetermined direction,
   means for scanning said plurality of light-responsive elements at increments of motion of the record across said field of view to develop a series of signals from each said element corresponding to intensity of light at each said element at each said increment, and
   means for electronically storing said plurality of signals.

2. The apparatus set forth in claim 1 wherein said signal-storing means comprises digital storage means, means responsive to said scanning means for digitizing said signals, and means for storing said digitized signals in said digital storage means.

3. The apparatus set forth in claim 2 wherein said signal-storing means further comprises means for normalizing said signals against variation in sensitivity of said light-responsive elements.

4. The apparatus set forth in claim 3 wherein said normalizing means comprises calibration means of uniform optical characteristics, means for selectively positioning said calibration means within said field of view at a position illuminated by said source, means responsive to signals from said array with said calibration means in said field of view to determine gain factors for each said signal as a function of differences among said signals, and means for multiplying each of said signals by associated gain factors prior to storage in said digital storage means.

5. The apparatus set forth in claim 4 further comprising means responsive to signals from said array with said calibration means in said field of view to identify background illumination noise, and means for offsetting said signals as a function of said background illumination noise prior to storage in said digital storage means.

6. The apparatus set forth in claim 1 wherein said camera further includes means forming an aperture through which said field of view is projected into said array, and wherein said apparatus further comprises means for selectively varying said aperture.

7. The apparatus set forth in claim 1 wherein said mounting means is constructed to move a record mounted thereon in a linear direction orthogonal to the direction of gel separation on the record.

8. The apparatus set forth in claim 7 wherein said light source and said camera are positioned on the same side of a record carried by said mounting means.

9. The apparatus set forth in claim 8 for analyzing separations stained with fluorescent dye, wherein said light source comprises an ultraviolet light source.

10. The apparatus set forth in claim 9 wherein said light source comprises a housing having a pair of optically aligned windows, said ultraviolet light source being positioned within said housing off-axis with respect to said windows, and reflective means within said housing for reflecting radiation from said source through one of said windows onto a gel separation record carried by said mounting means.

11. The apparatus set forth in claim 10 wherein said reflective means comprises elliptical reflective means.

12. The apparatus set forth in claim 10 wherein one of said windows spaced from said mounting means comprises means for blocking transmission of ultraviolet radiation to said camera.

13. The apparatus set forth in claim 10 wherein said camera further comprises filter means for blocking transmission of ultraviolet radiation to said linear array.

14. The apparatus set forth in claim 10 wherein said mounting means further includes means spaced from said enclosure for blocking emission of ultraviolet radiation transmitted through a gel separation record in said mounting means.

15. The apparatus set forth in claim 14 wherein said emissions-blocking means comprises an ultraviolet reflector.

16. The apparatus set forth in claim 14 wherein said emission-blocking means includes a window for observing fluorescence at a gel separation record carried by said mounting means.

17. Apparatus for analyzing an electrophoretic record that includes at least one gel separation, said apparatus comprising:
   a light source including an enclosure having an elongated narrow window, light emitting means, and means for directing light from said emitting means through said window,
   means for mounting an electrophoretic record adjacent to said window and for translating said record across said window in a predetermined linear direction orthogonal to direction of gel separation on the record such that said light source illuminates a narrow portion of the record lengthwise of the separation thereon,
   a camera including a plurality of light-responsive elements disposed in a linear array, and means for projecting an image of a record on said mounting means onto said camera such that said camera has a linear field of view of a portion of the gel separation record illuminated by said light source and orthogonal to said predetermined direction,
   means for scanning said light-responsive elements at increments of motion of the record across said window to develop a series of signals from each said light-responsive element corresponding to intensity of light at each said element at each said increment, and
   digital storage means including means responsive to said scanning means for digitizing said signals, and means for storing said digitized signals in digital memory as a function of said increments of translation.

18. The apparatus set forth in claim 17 wherein said projecting means includes means projecting said image onto said array through said window, said light emitting means being mounted off-axis with respect to said image such that said image excludes said light emitting means.

19. The apparatus set forth in claim 18 further comprising means spaced from said window to block emission of radiation from said light emitting means, said mounting means being constructed to translate a gel separation record past said window between said window and said blocking means.

20. The apparatus set forth in claim 19 further comprising calibration means having predetermined optical characteristics, means for selectively bringing said calibration means to a position adjacent to said window, and means for calibrating said digitizing means as a function of light energy received at said array with said calibration means adjacent to said window.

21. The apparatus set forth in claim 20 further comprising means responsive to signals from said array with said calibration means adjacent to said window to identify background illumination noise, and means for offsetting said signals as a factor of said background illumination noise prior to storage in said digital storage means.

22. The apparatus set forth in claim 19 wherein said emission-blocking means comprises means for reflecting light energy back into said window.

23. The apparatus set forth in claim 22 wherein said light-emitting means comprises a source of ultraviolet radiation.

24. A method of analyzing an electrophoretic record that includes at least one gel separation, said method comprising the steps of:
  (a) translating the record in a linear direction orthogonal to the gel separation thereon,
  (b) illuminating a narrow portion of the record in the direction of the separation thereon,
  (c) positioning a camera that includes a plurality of light-responsive elements disposed in a linear array such that said array has a field of view that includes an illuminated portion of the separation record,
  (d) scanning said array at increments of record translation to develop a series of signals from each element corresponding to intensity of light at each said element at each said scan increment,
  (e) digitizing said signals, and
  (f) storing the digitized sample in electronic memory.

25. The method set forth in claim 24 comprising the additional step of: (g) calibrating said step (e) by:
  (g1) placing means having known optical characteristics in said field of view,
  (g2) scanning said array as in said step (d) to develop a plurality calibration signals corresponding to intensity of light at each said element, and thereafter
  (g3) controlling said step (e) as a function of differences among said calibration signals.

26. The apparatus set forth in claim 17 further comprising means for positioning said camera means to obtained desired magnification of the record at said camera.

27. The apparatus set forth in claim 26 wherein said camera-positioning means comprises means for selecting predetermined magnification levels, and means for automatically positioning said camera in predetermined positions corresponding to said levels.

28. The apparatus set forth in claim 27 further comprising means responsive to said automatic positioning means for indicating position of said camera.

29. The apparatus set forth in claim 28 wherein said camera includes slide platforms carrying said array and said image-projecting means, stepper motors coupled to said slide platforms, and electronic control means responsive to said level-selecting means for controlling said motors.

30. The apparatus set forth in claim 17 wherein said record-translating means comprises means for selectively positioning said record-mounting means with respect to said light source.

31. The apparatus set forth in claim 31 wherein said record-translating means comprises a slide platform, a stepper motor coupled to said slide platform and control electronics coupled to said stepper motor, and wherein said selectively positioning means comprises means for selectively jogging said stepper motor.

* * * * *

UNITED STATES PATENT AND TRADEMARK OFFICE
CERTIFICATE OF CORRECTION

PATENT NO. : 4,960,999

DATED : October 2, 1990

INVENTOR(S) : Ronald A. McKean and Jeff Stiegman

It is certified that error appears in the above—identified patent and that said Letters Patent is hereby corrected as shown below:

Column 10, Line 37, change "claim 31" to -- claim 30 --.

Signed and Sealed this

Thirtieth Day of June, 1992

Attest:

DOUGLAS B. COMER

*Attesting Officer*     *Acting Commissioner of Patents and Trademarks*